(12) United States Patent
Julien et al.

(10) Patent No.: US 9,439,853 B2
(45) Date of Patent: Sep. 13, 2016

(54) FORM OF ADMINISTRATION OF ENKEPHALINASE INHIBITOR

(75) Inventors: Jean-Stëphane Julien, Saint Cyr sur Loire (FR); Marc Maury, Saint Medard en Jalles (FR); Jeanne-Marie Lecomte, Paris (FR); Xavier Ligneau, Saint Grégoire (FR); Philippe Robert, Pace (FR); Jean-Charles Schwartz, Paris (FR)

(73) Assignee: BIOPROJET, Paris (FR)

( * ) Notice: Subject to any disclaimer, the term of this patent is extended or adjusted under 35 U.S.C. 154(b) by 340 days.

(21) Appl. No.: 13/992,577

(22) PCT Filed: Dec. 9, 2011

(86) PCT No.: PCT/EP2011/072315
§ 371 (c)(1),
(2), (4) Date: Aug. 16, 2013

(87) PCT Pub. No.: WO2012/076691
PCT Pub. Date: Jun. 14, 2012

(65) Prior Publication Data
US 2013/0331423 A1   Dec. 12, 2013

(30) Foreign Application Priority Data
Dec. 10, 2010   (EP) .................................... 10306397

(51) Int. Cl.
| A61K 31/216 | (2006.01) |
| A61K 9/08 | (2006.01) |
| A61K 9/10 | (2006.01) |
| A61K 31/223 | (2006.01) |
| A61K 31/265 | (2006.01) |
| A61K 47/32 | (2006.01) |
| A61K 47/34 | (2006.01) |
| A61K 47/36 | (2006.01) |

(Continued)

(52) U.S. Cl.
CPC . *A61K 9/08* (2013.01); *A61K 9/10* (2013.01); *A61K 31/216* (2013.01); *A61K 31/223* (2013.01); *A61K 31/265* (2013.01); *A61K 31/4178* (2013.01); *A61K 47/32* (2013.01); *A61K 47/34* (2013.01); *A61K 47/36* (2013.01); *A61K 47/38* (2013.01)

(58) Field of Classification Search
None
See application file for complete search history.

(56) References Cited

U.S. PATENT DOCUMENTS

| 4,513,009 | A | 4/1985 | Roques et al. |
| 6,919,093 | B2 | 7/2005 | Lecomte et al. |
| 8,222,294 | B2 * | 7/2012 | Schwartz ............ A61K 31/265 514/305 |

(Continued)

FOREIGN PATENT DOCUMENTS

| FR | WO 0197803 A1 * | 12/2001 | ............ A61K 9/009 |
| WO | WO 01/97803 | 12/2001 | |
| WO | WO 2007/102171 | 9/2007 | |

OTHER PUBLICATIONS

XP-002666874 to Song et al., 2007.*

(Continued)

*Primary Examiner* — Svetlana M Ivanova
(74) *Attorney, Agent, or Firm* — B. Aaron Schulman, Esq.; Stites & Harbison, PLLC.

(57) ABSTRACT

The present invention relates to a new formulation of an enkephalinase inhibitor, such as racecadotril or dexecadotril, the process for the preparation thereof, and the use thereof in the treatment of diarrhea.

17 Claims, 3 Drawing Sheets

(51) Int. Cl.
    *A61K 47/38*     (2006.01)
    *A61K 31/4178*   (2006.01)

(56) References Cited

U.S. PATENT DOCUMENTS

2003/0108575 A1   6/2003   Lu
2007/0275993 A1   11/2007  Schwartz et al.
2010/0081697 A1   4/2010   Chao et al.

OTHER PUBLICATIONS

Hawkings Watts, The Effect of pH on Potassium Sorbate effectiveness, Dec. 7, 2009, available at http://www.hawkinswatts.com.au/documents/091207%20Potassium%20Sorbate%20pH.pdf.*

International Search Report for PCT/EP2011/072315 dated Jan. 13, 2012.

Database CA [Online] Chemical Abstracts Service, Columbus, Ohio, US; Song, Tian et al: "Preparation of racecadotril suspension and preliminary study on its stability", XP002666874, retrieved from STN, Database accession No. 2008:395801, Yiyao Daobao,26(1), 57-59 Coden: YDIAAL; ISSN: 1004-0781, 2007.

Database Medline [Online] US National Library of Medicine (NLM), Bethesda, MD, US; (Dec. 2006), Reddy K Mallikarjun et al: "Structural studies of racecadotril and its process impurities by NMR and mass spectroscopy.", XP9155466, Database accession No. NLM17283655, the whole document, DIE Pharmazie Dec. 2006 LNKD-PUBMED:17283655, vol. 61, No. 12, (Dec. 2006), pp. 994-998.

Merck Index, Ed 2006, p. 1392, "Racecadotril".

* cited by examiner

FORM OF ADMINISTRATION OF ENKEPHALINASE INHIBITOR

The present invention relates to a new formulation of an enkephalinase inhibitor, such as racecadotril or dexecadotril, the process for the preparation thereof, and the use thereof in the treatment of diarrhoea.

Racecadotril and dexecadotril are potent enkephalinase inhibitor with unique intestinal antisecretory activity. Racecadotril displays interesting antidiarrhea activity, including in infants and children. The compound is insoluble in water and, for these young patients, it has to be administered in the form of suspensions, the latter being prepared extemporaneously from a granulated powder as described in WO 01/97801; this constitutes the commercial paediatric formulation which has already been used by millions of patients since its development.

Nevertheless, this commercial paediatric formulation displays some disadvantages. First a posology in strict proportion with the age or weight of the children or infants, which is optimally required, cannot easily be respected when starting from a powder. The use of the powder to prepare suspensions requires multiple unity dosages, commercially presented in sachets containing different weights of racecadotril and which have to be used in variable number to prepare suspensions of strengths adapted to the age/weight of the young patients.

This introduces difficulties in the mode of preparation by the parents, in the remembering of the posology by the prescribing doctor and this leads to risks of errors. In addition, the price of such multiple formulations is inherently higher than that of e.g. a syrup, a form often used in paediatry. Further, the suspension made from resuspending the powder into water may require strong mixing and quick administration, to ensure that the full of the active ingredient is administered; else, the granules of racecadotril may settle so that the full dose is not administered to the patient. Finally, a strict posology according age/weight of patients cannot be respected with the current commercial paediatric formulation.

There is therefore a need to provide aqueous suspensions of enkephalinase inhibitors such as racecadotril or dexecadotril.

However, there has been a prejudice so far to provide aqueous suspensions of racecadotril in view of its bitter taste, and its degradation profile in aqueous media. In particular, one difficulty in preparing stable suspensions of racecadotril is the risk of hydrolysis of this compound which bears an ester group and can be easily hydrolyzed into easily oxidizable and less active compounds.

Antiemetic agents, such as 5-$HT_3$ receptor antagonists and in particular ondansetron and granisetron have been used with an enkephalinase inhibitor for the treatment of acute gastroenteritis, as disclosed in PCT/IB2005/000351. In practice, ondansetron is administered in the form of coated tablets, parenteral forms or suppositories for adults and in the form of parenteral forms or syrups for infants and children. It is therefore desirable to provide a single formulation to simultaneously administer both the enkephalinase inhibitor and the 5-HT3 receptor antagonist. However, an homogeneous powder mixing of two active principles with very different concentrations is generally difficult to obtain.

The present inventors have now surprisingly discovered that some aqueous suspensions of an enkephalinase inhibitor such as racecadotril or dexecadotril unexpectedly may fulfil the above requirements.

The formulation of the invention comprises a stable aqueous suspension of an enkephalinase inhibitor which can be conveniently administered in varying volumes according to the age or weights of infants or children. Furthermore, ondansetron being soluble in the water phase of the suspension, an homogeneous formulation can be easily obtained in spite of the large difference in concentrations of the two active principles.

The stable aqueous suspensions of the invention are made possible in particular by carefully adjusting the pH of the suspension. The aqueous suspensions of the invention unexpectedly show stability, improved oral bioavailability over the known suspension made up from the powder, and lack of toxicity in rodents.

According to a first object, the present invention thus concerns an aqueous suspension of an enkephalinase inhibitor suitable for oral administration, wherein said suspension has a pH comprised between 3.5 and 5.

Said enkephalinase inhibitor may be racecadotril or dexecadotril.

Said pH is preferably comprised between 4 and 4.5, more preferably between 4 and 4.2, still more particularly about 4.

Said pH may be achieved by the presence of suitable buffering agents able to adjust the pH of the aqueous suspension within the desired pH range, in particular sodium citrate, lactic acid including diluted lactic acid (e.g. 5% lactic acid) and/or their mixtures.

Said buffering agent is generally present in sufficient concentration so as to achieve the desired pH.

Said suspension generally comprises at least one thickening agent and/or suspending agent(s), preferably at least one thickening agent.

Said thickening agents may be chosen from cellulose and its derivatives such as hydroxyethylcellulose, hydroxypropylcellulose, methylcellulose, ethylcellulose, hydroxypropylmethylcellulose, carboxymethyl-cellulose, microcrystalline cellulose blends; synthetic polymers such as crosslinked polyacrylate, polyvinylpyrrolidone, polyvinyl alcohol, poloxamer and carbomers.

Said suspending agents may be chosen from sucrose; or other natural polymers such as alginates, gums including xanthan, guar, agar-agar, bean locust, acacia, tragacanth, carrageenan; clays such as magnesium aluminium silicate, aluminium metahydroxyde, bentonite, magnesium hectorite; ethoxylated isostearyl alcohols, polyoxyethylene sorbitol and sorbitan esters.

Preferably, the suspension of the invention comprises at least one cellulose derivative and at least one natural polymer; preferably hydroxyethylcellulose and xanthan gum.

The aqueous suspension of the invention may additionally comprise one component selected from the group comprising pharmaceutically acceptable carriers, diluents, adjuvants, excipients, or vehicles, such as preservatives, fillers, disintegrating agents, wetting agents, emulsifying agents, sweetening agents, flavoring agents, colouring agents, perfuming agents, antibacterial agents, antifungal agents.

Prevention of the action of microorganisms can be ensured by various antibacterial and antifungal agents, for example, parabens, chlorobutanol, phenol, sorbic acid, and the like.

Examples of suitable carriers, diluents, solvents or vehicles in addition to water include ethanol, polyols, suitable mixtures thereof, vegetable oils (such as olive oil).

Generally, the aqueous suspension of the invention comprises at least one preservative, in particular chosen from sodium benzoate, benzoic acid, sorbic acid and their salts, more preferably sodium benzoate.

Generally, the aqueous suspension of the invention comprises at least one sweetening agent such as sucrose.

Generally, the aqueous suspension of the invention comprises at least one flavouring agent such as artificial flavours.

The present invention further encompasses aqueous suspension as defined above additionally comprising ondansetron.

A typical aqueous suspension of the invention may comprise:
- at least one enkephalinase inhibitor: 2 to 5 g/l of suspension, preferably about 4 g/l;
- at least one thickening and/or suspending agent(s), preferably at least one thickening agent: 4 to 16 g/l of suspension;
- buffering agent so as to adjust to the desired pH.

It may additionally comprise one of the following ingredients:
- preservative: 1 to 6 g/l of suspension; and/or
- sweetening agent: 550 to 650 g/l of suspension; and/or
- flavouring agent: 0.8 to 5, preferably 0.8 to 1.2 g/l of suspension.

Particular aqueous suspensions of the invention may further comprise:
- ondansetron: 0.1 to 0.8 g/l of suspension, preferably 0.05 to 0.5, more preferably about 0.4 g/l.

The compositions can be prepared by any of the methods well known in the art of pharmacy. Such methods comprise mixing together the ingredients of the aqueous suspension and include the step of bringing into association the active ingredient with the carrier which constitutes one or more accessory ingredients. In general the compositions are prepared by uniformly and intimately bringing into association the active ingredient with liquid carriers or finely divided solid carriers or both, and then, if necessary, shaping the product.

The process of the invention comprises the step of adding a buffering agent to an aqueous suspension of an enkephalinase inhibitor so as to adjust the pH between 3.5 and 5.

The process of preparation may further comprise the preliminary steps of:
- optionally adding the optional sweetening agent and/or preservative to water;
- dispersing the enkephalinase inhibitor and at least one thickening and/or suspending agent(s) and the optional ondansetron, flavouring agent(s) and/or preservative(s) in water which may contain the optional sweetening agent.

Alternatively, the process of preparation may further comprise the preliminary steps of:
- dispersing the enkephalinase inhibitor with optional sweetening agent(s), flavouring agent(s), preservative(s) and/or ondansetron in water, and
- adding at least one thickening and/or suspending agent(s).

The dispersion may be stirred to obtain a final suspension.

The pH may be adjusted by mixing a first buffering agent with the enkephalinase inhibitor dispersion and then adding a second buffering agent to the final suspension.

Said dispersing is generally conducted under stirring, at a temperature comprised between room temperature and 70° C.

Preferably, said dispersing step is conducted following the step of dissolving any preservative into water.

The process may further comprise the additional step of homogenizing the size of the suspended particles by grinding the suspension.

According to another preferred aspect, the aqueous suspension of the invention allows the precise administration of 1.5 mg/kg of body weight which allows the administration of a dose of less that 6 mg for children or babies.

Generally, 2.5 ml of the aqueous suspension delivers the same dose (10 mg) of racecadotril as the commercially available sachet of coated granules of racecadotril.

According to another preferred aspect, the aqueous suspension of the invention allows the administration of 1 and 8 mg, preferably between 2 to 8 mg of ondansetron per dosage unit for adults of 0.2 to 4 mg for children or babies.

Generally, 2.5 ml of the aqueous suspension delivers from 0.25 mg to 2 mg of ondansetron, preferably about 0.5 mg of ondansetron.

In accordance with another subject-matter, the present invention also relates to aqueous suspensions of enkephalinase inhibitor for use for the treatment and/or prevention of diarrhoea, and/or acute gastroenteritis.

According to a preferred aspect, when the aqueous suspension further comprises ondansetron, the invention also concerns said aqueous suspension for use for the treatment and/or prevention of acute diarrhoea associated with emesis.

According to a still preferred aspect, said diarrhoea is chemotherapy-induced diarrhoea, carcinoid diarrhoea, traveller's diarrhoea, diarrhoea elicited by various bacteria, viruses or parasites in adults, children or babies.

According to another preferred aspect, said treatment comprises oral administration, preferably two to four times a day.

Figure 1:
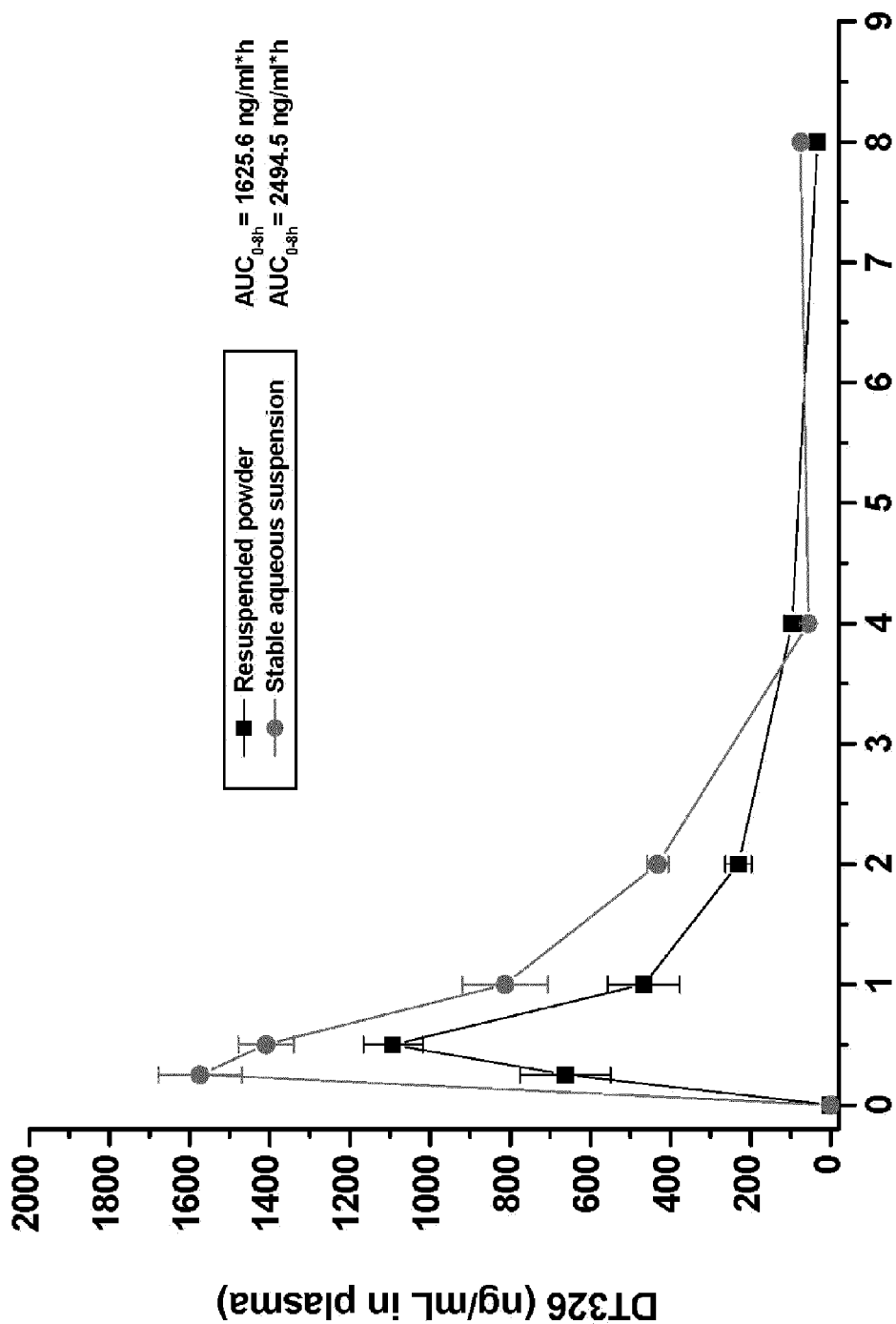
FIG. 1 illustrates the pharmacokinetic profile of the biologically active moiety of racecadotril after oral administration of the aqueous suspension of racecadotril (48 mg/kg) in Swiss male mice (n=4).

The following examples are provided as a non-limiting illustration of the present invention.

EXAMPLE 1

Preparation of an Aqueous Suspension of Racecadotril

As per 500 mL of Oral Suspension:

In 175 mL of purified water, 2.500 g of sodium benzoate were slowly added under stirring until complete dissolution. The solution was heated to about 60° C. under continuous stirring and 300.000 g sucrose were added. While continuing stirring slowly, the solution was then cooled down to about 30° C. and the following materials were slowly added under high-speed dispersion:

| | |
|---|---|
| Racecadotril | 2.000 g |
| Xanthan gum | 2.500 g |
| Hydroxyethylcellulose | 2.500 g |
| Strawberry flavor | 0.500 g |

Slow stirring was maintained for about 30 minutes, and then under slow mixing 3.750 g of sodium citrate were added. Slow stirring was continued for about 20 minutes. The pH of the so obtained suspension was then adjusted to 4.0 with a lactic acid solution 5% m/v. The final volume (500 mL) of the suspension was adjusted while continuing slowly stirring with purified water.

| Constituent | Quantity (unit formula) | Quantity (as per 100 ml of oral suspension) | Fonction |
|---|---|---|---|
| Racecadotril | 0.16000 g | 0.4000 g | Active ingredient |
| Excipients: | | | |
| Sodium benzoate | 0.20000 g | 0.5000 g | Preservative |
| Hydroxy-ethylcellulose | 0.20000 g | 0.5000 g | Thickening agent |
| Xanthan gum | 0.20000 g | 0.5000 g | Suspending agent |
| Strawberry flavour | 0.04000 g | 0.1000 g | Flavoring agent |
| Sucrose | 1.50000 g | 60.0000 g | Sweetening and suspending agent |
| Sodium citrate | 0.30000 g | 0.7500 g | Buffering agent |
| Lactic acid | QS pH 4.0 ± 0.2 | QS pH 4.0 ± 0.2 | Buffering agent |
| Purified water | QS 40 mL | QS 100 mL | Solvent |

EXAMPLE 2A

Aqueous Suspension of Racecadotril/Ondansetron

As per 500 mL of Oral Suspension:

In 175 mL of purified water, 2.500 g of sodium benzoate were slowly added under stirring until complete dissolution. The solution was heated to about 60° C. under continuous stirring and 300.000 g sucrose were added. While continuing stirring slowly, the solution was then cooled down to about 30° C. and the following materials were slowly added under high-speed dispersion:

| Racecadotril | 2.000 g |
|---|---|
| Ondansetron | 0.100 g |
| Xanthan gum | 2.500 g |
| Hydroxyethylcellulose | 2.500 g |
| Strawberry flavor | 0.500 g |

Slow stirring was maintained for about 30 minutes, and then under slow mixing 3.750 g of sodium citrate were added. Slow stirring was continued for about 20 minutes. The pH of the so obtained suspension was then adjusted to 4.0 with a lactic acid solution 5% m/v. The final volume (500 mL) of the suspension was adjusted while continuing slowly stirring with purified water.

| Constituent | Quantity (unit formula) | Quantity (as per 100 ml of oral suspension) | Fonction |
|---|---|---|---|
| Racecadotril | 0.16000 g | 0.4000 g | Active ingredient |
| Ondansetron | 0.008000 | 0.0200 g | Active ingredient |
| Excipients: | | | |
| Sodium benzoate | 0.20000 g | 0.5000 g | Preservative |
| Hydroxy-ethylcellulose | 0.20000 g | 0.5000 g | Thickening agent |
| Xanthan gum | 0.20000 g | 0.5000 g | Suspending agent |
| Strawberry flavour | 0.04000 g | 0.1000 g | Flavoring agent |
| Sucrose | 1.50000 g | 60.0000 g | Sweetening and suspending agent |
| Sodium citrate | 0.30000 g | 0.7500 g | Buffering agent |
| Lactic acid | QS pH 4.0 ± 0.2 | QS pH 4.0 ± 0.2 | Buffering agent |
| Purified water | QS 40 mL | QS 100 mL | Solvent |

EXAMPLE 2B

Aqueous Suspension of Racecadotril/Ondansetron

As per 2 500 L of Oral Suspension

In about 315 L of purified water, 1 500 kg of sucrose in solution at about 67% were added under stirring. Under continuous stirring introduce until complete dissolution/dispersion:

| Sodium benzoate | 7.50 kg |
|---|---|
| Ondansetron | 0.5 kg |
| Racecadotril | 10 kg |
| Hydroxethylcellulose | 12.50 kg |
| Xanthan gum | 12.50 kg |
| Sodium citrate | 18.75 kg |
| Strawberry flavor | 7.70 kg |

Then, under stirring, adjust the pH of the so obtained suspension within 4.0 to 4.2 with a lactic acid solution 60% m/v.

Adjust final volume (2 500 L) of the suspension with purified water while continuing stirring.

Homogenize size of particles suspended by continuous grinding of the suspension for 8 hours, then heat the suspension to a temperature of 40° C. under slow stirring and under vacuum to allow air bubbles to migrate out of the suspension.

EXAMPLE 3

Pharmacokinetic Profile

Racecadotril was orally administered (48 mg/kg) to 24 mice (n=4 per value) in the form of powder resuspended in water and in the form of the aqueous suspension of example 1. The concentration of the active moiety of racecadotril (DT326) in plasma is measured. Results are illustrated in FIG. 1. They show that the bioavailability of racecadotril when administered in the aqueous suspension is increased by 50% in comparison of that when administered in the form of powder resuspended in water.

EXAMPLE 4

Stability

The pH of the suspensions of example 1 (10 mg racecadotril/2.5 mL) and 2 (10 mg racecadotril/1 mg ondansetron/2.5 ml) was adjusted to 4, 4.5 and 5. The three samples for each suspension were stored under the following accelerated conditions at 40° C./75% relative humidity during 6 weeks.

Figure 2:
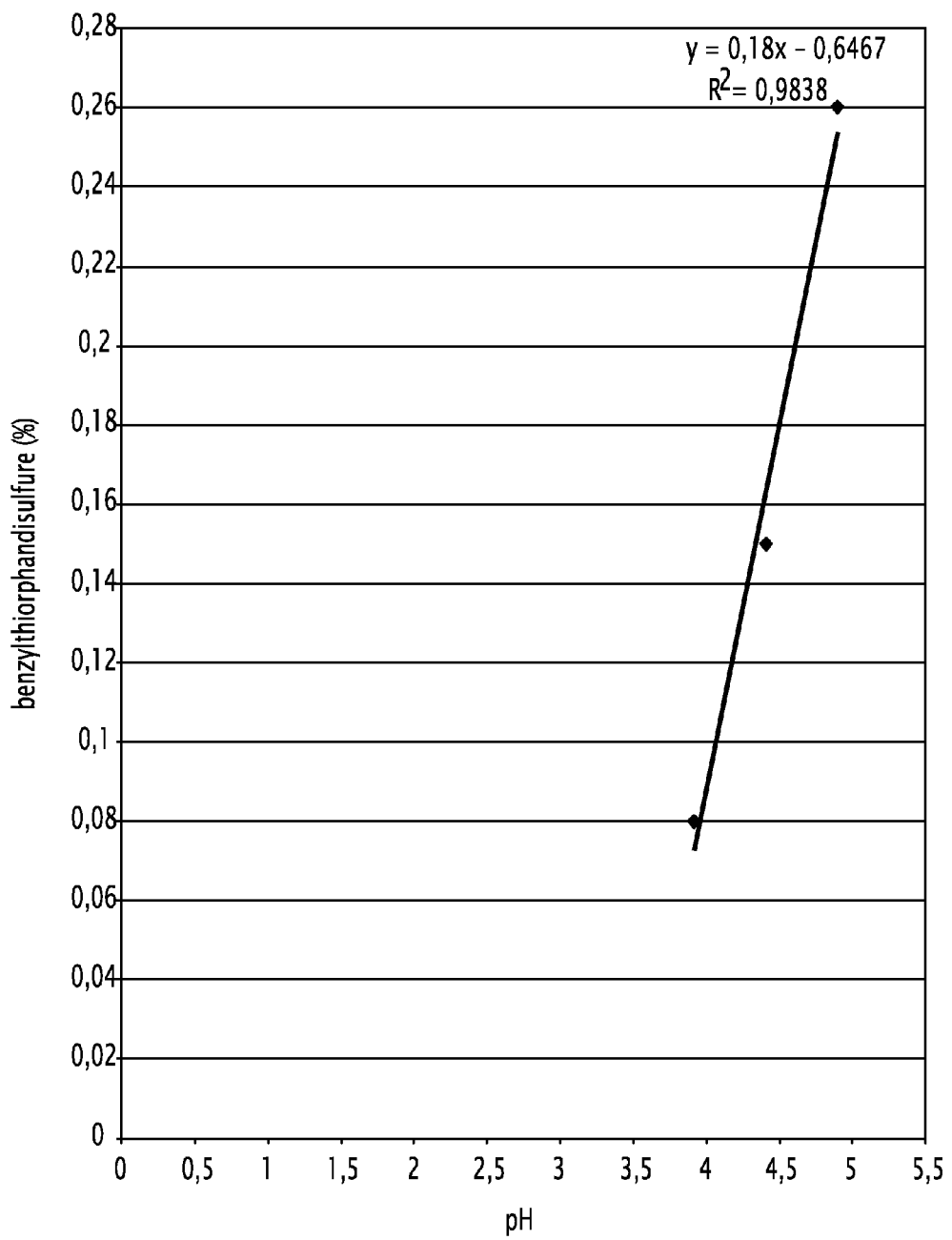
FIG. 2 illustrates the stability of the aqueous suspension of racecadotril (10 mg/2.5 mL) and shows the effect of the pH of the aqueous suspension of racecadotril on the concentration of a degradation product of racecadotril (benzylthiorphandisulfure).
Figure 3:
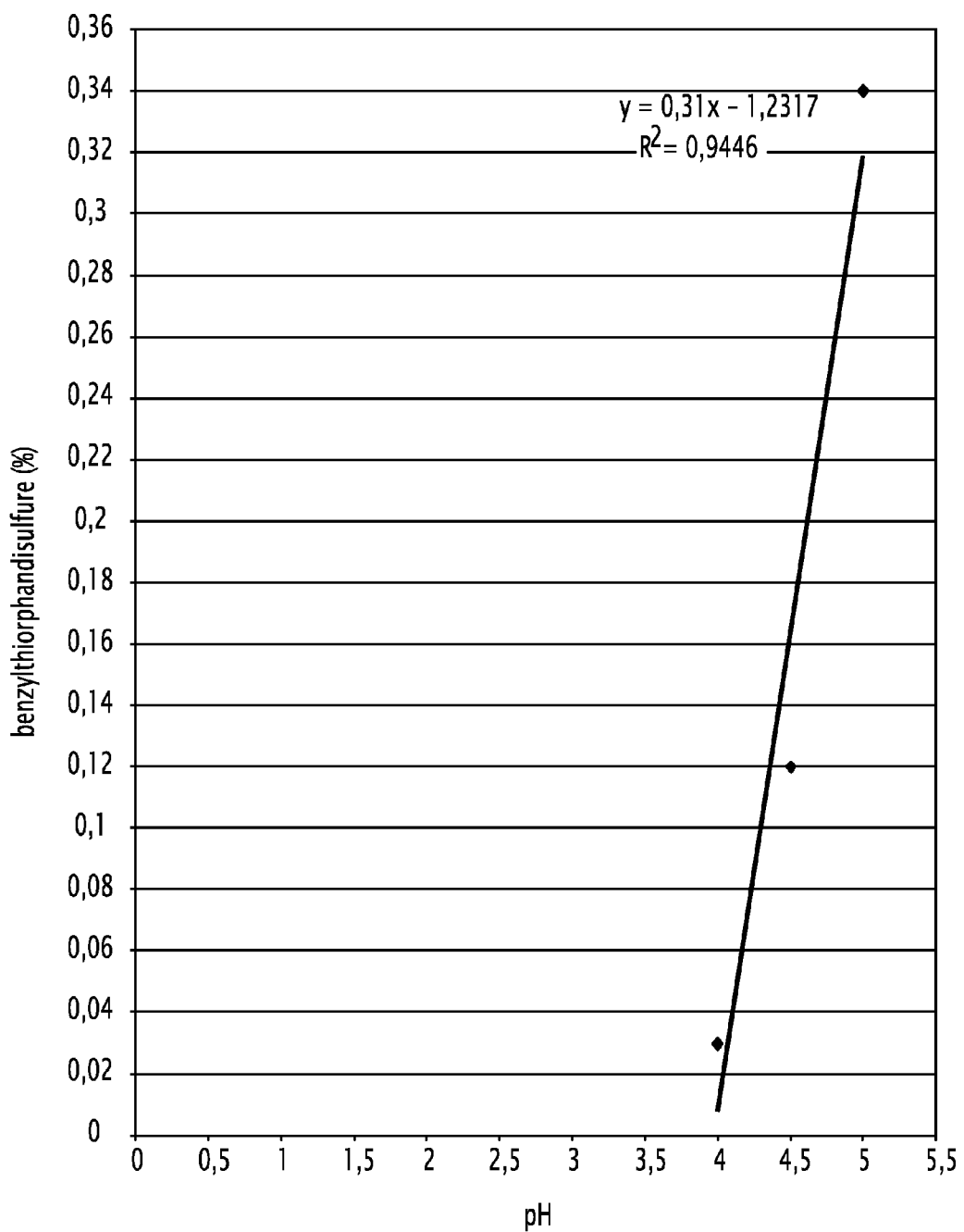
FIG. 3 illustrates the stability of the aqueous suspension of racecadotril and ondansetron (10 mg/1 mg/2.5 mL) and shows the effect of the pH of the aqueous suspension of racecadotril/ondansetron on the concentration of a degradation product of racecadotril (benzylthiorphandisulfure) appearing upon storage.

Following the storage, the % of a degradation product of racecadotril (benzylthiorphandisulfure) was measured for each value of the pH. Results are illustrated in FIGS. 2 and 3. They show that the degradation unexpectedly decreases as the pH decrease, as hydrolysis generally increases in acidic conditions. In view of these results and the racecadotril specification, an optimal range of pH comprised between 3.5 and 5 may be considered.

EXAMPLE 5

Particle Size Distribution Profile of the Suspension

Particle size distribution profile of racecadotril in suspension obtained in example 2b was determined using laser diffraction measurement and shows a bimodal distribution corresponding to 50% of particles in volume within 1 μm to about 70 μm with the upper limit of about 750 μm. This profile is advantageous in that the suspension exhibit both improved bioavailability (with the smaller particles) and stability (with the larger particles).

The invention claimed is:

1. An aqueous suspension comprising an enkephalinase inhibitor, said aqueous suspension being suitable for oral administration, wherein said aqueous suspension has a pH between 3.5 and 5, wherein said enkephalinase inhibitor is racecadotril or dexecadotril.

2. The aqueous suspension according to claim 1, wherein said pH is between 4 and 4.5.

3. The aqueous suspension according to claim 1 further comprising one or more buffering agent(s).

4. The aqueous suspension according to claim 3, wherein said buffering agent is selected from the group consisting of sodium citrate, lactic acid and their mixtures.

5. The aqueous suspension according to claim 1 further comprising one or more thickening and/or suspending agent(s).

6. The aqueous suspension according to claim 5, wherein said thickening and/or suspending agent is selected from the group consisting of cellulose and its derivatives, said derivatives selected from the group consisting of hydroxyethylcellulose, hydroxypropylcellulose, methylcellulose, ethylcellulose, hydroxypropylmethylcellulose, carboxymethylcellulose, and microcrystalline cellulose blends; synthetic polymers selected from the group consisting of crosslinked polyacrylate, polyvinylpyrrolidone, polyvinyl alcohol, poloxamer and carbomers; sucrose; natural polymers selected from the group consisting of alginates, gums including xanthan, guar, agar-agar, bean locust, acacia, tragacanth, and carrageenan; clays selected from the group consisting of magnesium aluminium silicate, aluminium metahydroxyde, bentonite, and magnesium hectorite; ethoxylated isostearyl alcohols, polyoxyethylene sorbitol and sorbitan esters; and mixtures thereof.

7. The aqueous suspension according to claim 6, wherein said thickening and/or suspending agent(s) are selected from the group consisting of hydroxyethylcellulose, xanthan gum, and mixtures thereof.

8. The aqueous suspension according to claim 1 further comprising at least one preservative.

9. The aqueous suspension according to claim 8 wherein said preservative is selected from the group consisting of sodium benzoate, benzoic acid, sorbic acid and their salts.

10. The aqueous suspension according to claim 1 further comprising at least one sweetening agent and/or flavouring agent.

11. The aqueous suspension according to claim 1 further comprising ondansetron.

12. The aqueous suspension according to claim 1 comprising:
at least one enkephalinase inhibitor: 2 to 5 g/l of suspension;
at least one thickening and/or suspending agent(s): 4 to 16 g/l of suspension;
buffering agent so as to adjust pH between 3.5 and 5.

13. The aqueous suspension according to claim 1 further comprising one or more of the following ingredients:
preservative: 1 to 6 g/l of suspension; and/or
sweetening agent: 550 to 650 g/l of suspension; and/or
flavouring agent: 0.8 to 5 g/l of suspension.

14. The aqueous suspension according to claim 1 further comprising:
ondansetron: 0.1 to 0.5 g/l of suspension.

15. A process of preparation of the aqueous suspension according to claim 1 comprising the step of adding a buffering agent to an aqueous suspension of said enkephalinase inhibitor so as to adjust the pH between 3.5 and 5.

16. An aqueous suspension of said enkephalinase inhibitor according to claim 1 for use for the treatment and/or prevention of diarrhoea, acute gastroenteritis, and/or acute diarrhoea associated with emesis.

17. An aqueous suspension of enkephalinase inhibitor claim 1 for use for the treatment and/or prevention of diarrhea, acute gastroenteritis, and/or acute diarrhea associated with emesis.

* * * * *